US00PP11142P

United States Patent [19]

van Andel

[11] Patent Number: Plant 11,142

[45] Date of Patent: Dec. 7, 1999

[54] ALSTROEMERIA PLANT NAMED 'STAPRISTEF'

[75] Inventor: Jacob van Andel, Aalsmeer, Netherlands

[73] Assignee: Staaveren, B.V., Aalsmeer, Netherlands

[21] Appl. No.: 09/021,492

[22] Filed: Feb. 10, 1998

[51] Int. Cl.[6] ..... A01H 5/00

[52] U.S. Cl. ..... Plt./309

[58] Field of Search ..... Plt./309

*Primary Examiner*—Howard J. Locker

*Attorney, Agent, or Firm*—Christie, Parker & Hale, LLP

[57] ABSTRACT

A new and distinct Alstroemeria plant variety producing flowers of good quality and attractive coloration.

1 Drawing Sheet

BACKGROUND OF THE INVENTION

The present invention relates to a new and distinct variety of Alstroemeria which is a cross of two unnamed, undistributed varieties identified as seed parent 91D185-5 and as pollen parent 87G10692. The varietal denomination of the new variety is 'Stapristef'.

The first act of asexual reproduction of 'Stapristef' was in Aalsmeer, The Netherlands, by propagation by dividing rootstocks. Asexual reproduction by dividing rhizomes and tissue culture through successive generations in Aalsmeer, The Netherlands, has demonstrated that the combination of characteristics as herein disclosed for 'Stapristef' are firmly fixed and retained through successive generations.

SUMMARY OF THE INVENTION

The new variety of Alstroemeria, 'Stapristef', produces long lasting flowers of unusual coloration, as described herein.

DESCRIPTION OF ILLUSTRATION

The new variety of Alstroemeria hybrid is illustrated in the accompanying illustration, which shows typical flower characteristics, with colors being as nearly true as is possible for illustrations of this type.

DETAILED DESCRIPTION OF THE NEW VARIETY

The following is a detailed description of the new cultivar of Alstroemeria hybrid plants about one year old as observed in a greenhouse in Aalsmeer, The Netherlands on the month of October. Color designations indicated are in accordance with The Royal Horticultural Society Colour Chart by color plate designations.

'Stapristef' has not been observed under all possible environmental conditions. Phenotypic expression may vary with variations in environment such as temperature, light intensity, day length and growing and cultural conditions.

Botanical classification:

*Family.*—Amaryllidaceae.

*Genus.*—Alstroemeria sp.

*Commercial.*—Alstroemeria hybrid. Seedling.

Origin:

PLANT

Form: Bush, useful as pot plant and garden decoration.

Shape: Upright.

Height: About 25 to 45 cm.

Branching Characteristics: Flower stems to not branch

Blooming habit: Recurrent—From April up to and including October in the Netherlands.

Disease resistance: Unknown.

Foliage:

*Quantity.*—Abundant.

*Number of leaves.*—About 25 to 30.

*Size of leaf.*—Length About 3 to 10 cm. Width: About 1 to 2 cm.

*Shape of leaf.*—Elliptic.

*Margin.*—Minutely crimped.

*Texture.*—Glossy.

*Color.*—Upper side: Near 137A. Underside: Near 137C.

Venation: Curved

Rhizomes:

*Color.*—Near 155 D.

*Size.*—About 10 to 25 cm.

FLOWER

Size (when first anthers release pollen):

*Diameter.*—About 6 to 7 cm.

*Depth.*—About 4 to 5 cm.

Borne: Singly along simple racemes.

Shape:

*When bloom first opens.*—Cup.

*When bloom matures.*—Cup.

Fragrance: None.

Lasting quality:

*On plant.*—About 21 days.

*As cut flower.*—About 14 days

Discoloration after full bloom: No.

Tepals: (2)

*Number of tepals.*—About 6.

*Arrangement.*—2 concentric circles of 3 tepals.

*Shape.*—Tepals — obovate; bloom — cup shaped.

*Margin.*—Slightly serrated.

*Apex.*—Pointed.

*Size of bloom fully expanded.*—Diameter about 6 to 7 cm, depth about 4 to 5 cm.

*Texture.*—Soft.

*Color.*—Outer tepals, central area near 53B, entire tepal except central area near 56C, no stripes; inner lateral tepals have spots near 53B and a dark yellow center near 13A; between the red tip and the yellow center there is a white spot near 155D; inner lateral tepals have about 20–30 spots near 185A; inner median tepal has a red tip near 53B and a white section near 155 D; inner median tepal has about 5–15 spots, near 185A.

Peduncle or flower stem:

*Length.*—Pedicel about 2 to 3 cm, peduncle about 2 to 6 cm.

*Diameter.*—About 0.5 cm.

*Color.*—Near 137A.

*Strength.*—Strong.

*Number of blooms/stem.*—About 2 to 3, very small.

*Hairy.*—No.

Persistence Flower does not hang on and dry.

BUD

Size:

*Diameter.*—About 0.5 to 1.0 cm.

*Depth or length.*—About 1 to 2 cm.

Form: Pear-shaped.

Rate of opening: Fast.

Color of tepals:

*When tepals begin to unfurl.*—Near 53B.

REPRODUCTIVE ORGANS

Stamen:

*Number.*—About 6.

*Arrangement.*—About the style.

Anthers

*Size.*—About 0.5 to 1.0 cm.

*Color.*—Near 152C.

Filaments

*Length.*—About 5 cm.

*Color.*—Near 54B.

Pollen

*Color.*—Near 152A.

Pistils 1.

*Styles.*—Length about 4 to 6 cm.

*Color.*—Near 54B.

Stigmas:

*Color.*—Near 56C.

FRUIT

Fertile: Yes.

Shape: Round.

Color at maturity: Near 164A.

I claim:

1. A new Alstroemeria plant of the variety substantially as shown and described.

* * * * *

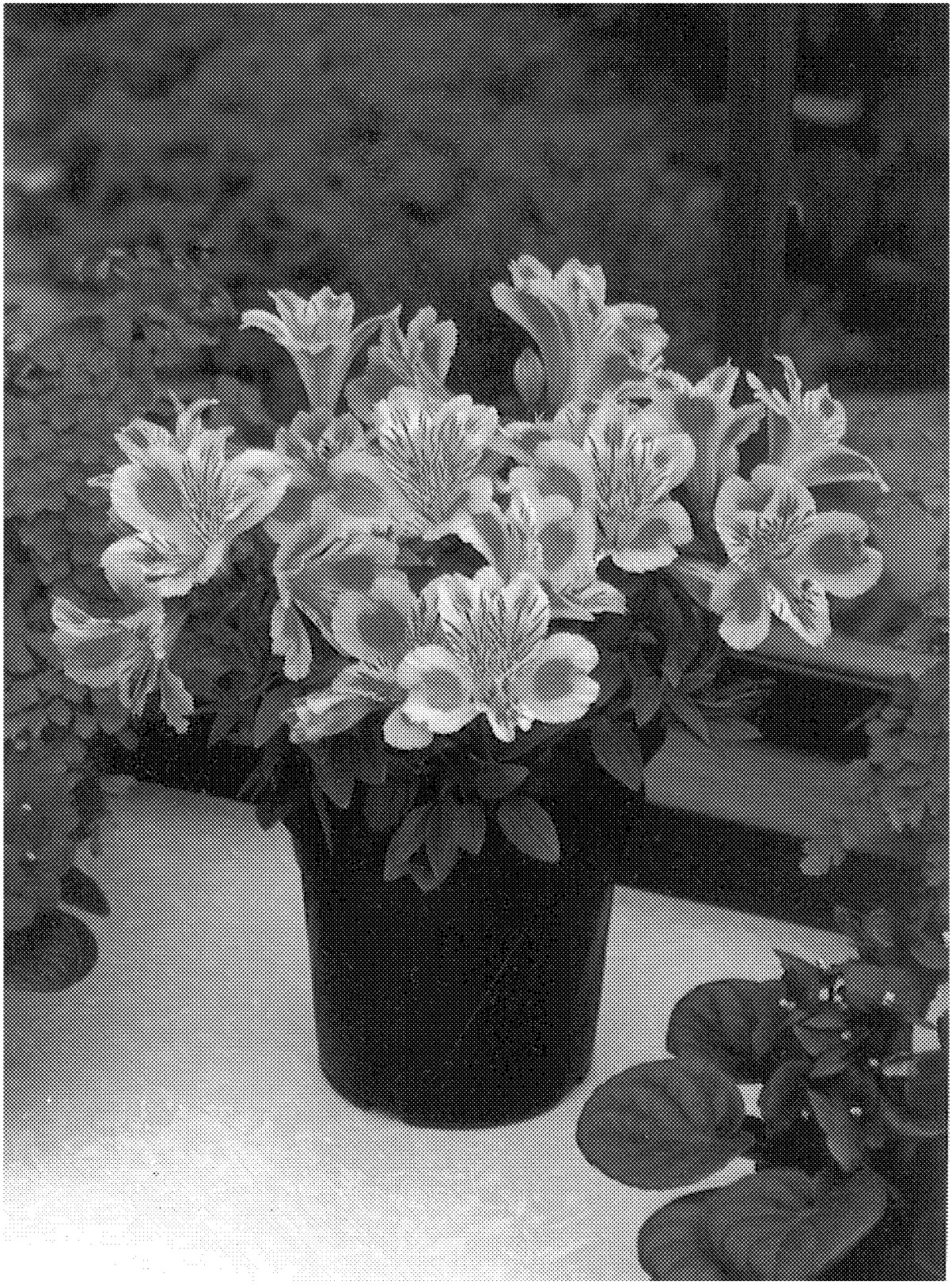

UNITED STATES PATENT AND TRADEMARK OFFICE

CERTIFICATE OF CORRECTION

PATENT NO. : PP11,142
DATED : December 7, 1999
INVENTOR(S) : Jacob van Andel

It is certified that error appears in the above-identified patent and that said Letters Patent is hereby corrected as shown below:

Title page,
Item [73] Assignee, the Assignee should read:
-- Van Staveren, B.V. Aalsmeer
Netherlands --

Signed and Sealed this

Twentieth Day of November, 2001

*Attest:*

Nicholas P. Godici

*Attesting Officer*

NICHOLAS P. GODICI
*Acting Director of the United States Patent and Trademark Office*